United States Patent [19]

Ono et al.

[11] Patent Number: 4,833,127

[45] Date of Patent: May 23, 1989

[54] NOVEL CSF AND METHOD FOR OBTAINING THE SAME

[75] Inventors: Masayoshi Ono, Saitama; Hitoshi Nomura, Tokyo, both of Japan

[73] Assignee: Chugai Seiyaku Kabushiki Kaisha, Tokyo, Japan

[21] Appl. No.: 754,287

[22] Filed: Jul. 12, 1985

[30] Foreign Application Priority Data

Jul. 25, 1984 [JP] Japan ................................ 59-153273

[51] Int. Cl.$^4$ ........................ A61K 37/02; C67K 15/16
[52] U.S. Cl. .................................... 514/21; 530/351; 530/395
[58] Field of Search ...................... 530/350, 395, 351; 514/21

[56] References Cited

U.S. PATENT DOCUMENTS

| | | | |
|---|---|---|---|
| 4,135,975 | 1/1979 | Liehtman et al. | 435/240.23 |
| 4,230,697 | 10/1980 | Nishida et al. | 530/395 |
| 4,342,828 | 8/1982 | Takaku et al. | 435/240.2 |
| 4,438,032 | 3/1984 | Giolde et al. | 530/351 |

FOREIGN PATENT DOCUMENTS

| | | |
|---|---|---|
| 118915 | 9/1984 | European Pat. Off. . |
| 169566 | 1/1986 | European Pat. Off. . |
| 183350 | 6/1986 | European Pat. Off. . |
| 54-140789 | 1/1979 | Japan . |
| 57-114525 | 7/1982 | Japan . |
| 59-078122 | 5/1984 | Japan . |
| WO85/04188 | 9/1985 | PCT Int'l Appl. . |
| WO86/00639 | 1/1986 | PCT Int'l Appl. . |
| WO86/04605 | 8/1986 | PCT Int'l Appl. . |

OTHER PUBLICATIONS

Gasson et al, Science, vol. 226, (1984), pp. 1339–1342.
Welte et al, "Purification and Biochemical Characterization of Two Differentiation Inducing Proteins for Leukemic Cells Produced by the Bladder Carcinoma Cell Line 5637", Leukemia: Recent Advances in Biology and Treatment, pp. 339–347 (Nov. 1985), presented in Jan.–Feb. 1985.

Gough et al, Nature, vol. 309, Jun. 28, 1984, pp. 763–767.
Begley et al, Exp. Hematol., vol. 13 (1985), pp. 956–962.
Nicola, Methods in Enzymology, vol. 116 (1985), pp. 600–619.
D. Metcalf, Blood, The Journal of The American Society of Hematology, vol. 67, No. 2 (Feb. 1986), pp. 257–267.
Erickson-Miller et al, Exp. Hematology, 16:184–189 (1988).
Strife et al, Blood, vol. 69, No. 5 (May 1987), pp. 1508–1523.
Lu et al, Cancer Research 46, pp. 4357–4361, Sep. 1986.
Welte et al, J. Exp. Med., The Rockefeller University Press, vol. 165 (Apr. 1987), pp. 941–948.
Asano et al, Abstract: "Characterization of Human Granulopoietic Colony–Stimulating Factors (hGCSF) Produced by Human Malignant Cells".
XVII Congress of the International society of Hematology; XV Congress of the International Society of Blood Transfusion; (Jul. 1978).
Migliaccio et al, Hematopoietic Colony Growth in Serum–Deprived Culture, Grune & Stratton, Inc., Jul. 1988, pp. 248–256.
Okabe et al, publication (1978), "Studies on the CSF–Producing Tumor(V)–Establishment of A Tissue Culture Strain (T3M-1) of Human CSF-Producing Tumor".

(List continued on next page.)

Primary Examiner—Delbert R. Phillips
Attorney, Agent, or Firm—Morgan & Finnegan

[57] ABSTRACT

A novel colony stimulating factor (CSF) that has the ability to promote the differentiation and proliferation of human bone marrow cells to neutrophiles, and a method for obtaining the same are disclosed. This CSF is produced from a novel cell line which has been established from tumor cells in patients with oral cancer.

This CSF has the potential for use only as a curative for leukopenia but also as a reagent for clinical testing and research studies.N

5 Claims, 4 Drawing Sheets

OTHER PUBLICATIONS

Abstract: Gabrilove et al, Experimental Hematology, vol. 12, No. 6, (Jul. 1984), p. 375.
Abstract: Welte et al, Experimental Hematology, vol. 12, No. 6, (Jul. 1984), p. 415.
Bradley et al, Aust. J. Exp. Biol. Med. Sci (1966), vol. 44, pp. 287-300.
Messner et al, Blood, vol. 42, No. 5 (Nov.), 1973 pp. 701-710.
Metcalf, Hemopoietic Colonies, In Vitro Cloning of Normal and Leukemic Cells, Springer-Verlag, Berlin, Heidelberg, New York, 1977, pp. 1-81, 123-125, 200-205 (partial text).
Burgess et al, Blood, vol. 49, No. 4 (Apr.), 1977, pp. 573-583.
Stanley et al, J. Biol. Chem., vol. 252, 1977, pp. 4305-4312.
Burgess et al, J. Biol. Chem., vol. 252, 1977, pp. 1998-2003.
Asano et al, Blood, vol. 49, No. 5 (May) 1977, pp. 845-852.
DiPersio et al, Blood, vol. 51, No. 3 (Mar.) 1978, pp 507-519.
Golde et al, Blood, vol. 52, No. 5 (Nov.) 1978, pp. 1068-1072.
Okabe et al, Cancer Research, vol. 38, Nov. 1978, pp. 3910-3917.
Stanley, Proc. Natl. Acad. Sci. USA, vol. 76, No. 6, Jun. 1979, pp. 2969-2973.
Ming-chi-Wu et al, J. Biol. Chem., vol. 254, 1979, pp. 6226≠6228.
Nicola et al, Blood, vol. 54, No. 3 (Sep.) 1979, pp. 614-627.
Burgess et al, In. J. Cancer, vol. 26, (1980), pp. 647-654.
DiPersio et al, Blood, vol. 56, No. 4 (Oct.) 1980, pp. 717-727.
Metcalf et al., Int. J. Cancer, vol. 30, 1982, pp. 773-780.
Das et al, J. Cellular Physiology, vol. 104, (1980), pp. 359-366.
Lee, M. and Hopkins, L. E., Am. J. Hospital Pharmacy, vol. 37, 1066-1071 (1980).
Ming-Chi Wu et al, J. Clin. Invest., vol. 65, Mar. 1980, pp. 772-775.
Welte et al., Abstract "Purification and Biochemical Characterization of Human Pluripotent Hematopoietic Colony-Stimulating Factor Produced by A Human Bladder Carcinoma Cell Line", Abstracts from Fourth International Lymphokine Workshop, Molecular and Cellular Biology of Lymphokines, Oct. 17-21, 1984 (Presented in Sep. 1984).
Lusis et al, Blood, vol. 57, No. 1 (Jan.), 1981, pp. 13-21.
Nicola et al, J. Cellular Physiology, vol. 112 (1982), pp. 257-264.
Metcalf, D., Natl. Cancer Institute Monograph No. 60, (1982), pp. 123-131.
Metcalf, D., Int. J. Cancer, vol. 30, (1982), pp. 203-210.
Okabe et al, J. Cellular Physiology, vol. 110, (1982), pp. 43-49.
Okabe et al, J.N.C.I., vol. 69, No. 6, Dec. 1982, pp. 1235-1243.
Schlunk et al, Blut, (1983), vol. 47, pp. 211-223.
Vadas et al, J. of Immunology, vol. 130, No. 2, Feb. 1983, pp. 795-799.
Ihle et al, J. of Immunology, vol. 131, No. 1 (1983), pp. 282-287.
Lopez et al, J. of Immunology, vol. 131, No. 6, Dec. 1983, pp. 2983-2988.
Nicola et al, J. Biol. Chem., vol. 258, (1983), pp. 9017-9023.
Clark-Lewis et al, J. Biol. Chem., vol. 259 (1984), pp. 7488-7492.
Welte et al, J. Cellular Biochemistry, Supplement 9A, 1985, p. 116.
Wong et al, Science, vol. 228 (1985), pp. 810-815.
Jubinsky et al, Proc. Natl. Acad. Sci, USA, vol. 82, May 1985, pp. 2764-2768.
Nicola et al, Nature, vol. 314, Apr. 18, 1985, pp. 625-628.
Welte et al, Proc. Natl. Acad. Sci. USA, vol. 82, Mar. 1985, pp. 1526-1530.
Nomura et al, EMBO Journal, vol. 5 (1986), pp. 871-876.
Gabrilove et al, Proc. Natl. Acad. Sci. USA, vol. 83, Apr. 1986, pp. 2478-2482.
Souza et al, Science, vol. 232, Apr. 1986, pp. 61-65.
Weinstein et al, Proc. Natl. Acad. Sci. USA, vol. 83 (1986), pp. 5010-5014.
Metcalf, Leukemia Research, vol. 7, No. 2 (1983), pp. 117-132.

(List continued on next page.)

OTHER PUBLICATIONS

Metcalf et al, Leukemia Research, vol. 9, No. 1 (1985), pp. 35–50.
Abboud et al, Blood, vol. 58, No. 6 (Dec.) 1981, pp. 1148–1154.
Vadas et al, J. Immunology, vol. 133, No. 1, Jul. 1984, pp. 202–207.
Lee et al, Proc. Natl. Acad. Sci. USA, vol. 82, Jul. 1985, pp. 4360–4364.
Tsuneoka et al, Cell Structure and Function, vol. 9 (1984), pp. 67–81.
Shah et al, Blood, vol. 50, No. 5 (Nov.), 1977, pp. 811–821.
Fojo et al, Biochemistry, vol. 17, No. 15 (1978), pp. 3109–3116.
Motoyoshi et al, Blood, vol. 52, No. 5 (Nov.), 1978, pp. 1012–1020.
Waheed et al, J. Lab. Clin. Med., Jul. 1979, vol. 94, No. 1, pp. 180–194.
Neumeier et al, Blut (1982), vol. 44, pp. 21–27.
Waheed et al, Blood, vol. 60, No. 1, (Jul.), 1982, pp. 238–244.
Yee-Pang Yung et al, J. of Immunology, vol. 129, No. 3, Sep. 1982, pp. 1256–1261.
Neumeier et al, Hoppe–Seyler's Z. Physiol. Chem., vol. 363, Dec. 1982, pp. 1493–1500.
Metcalf et al, J. Cellular Physiology, vol. 116, (1983), pp. 198–206.
Fung Fang Wang et al, J. Cellular Biochemistry, vol. 21, (1983), pp. 263–275.
Gerson et al, Blood, vol. 63, No. 4 (Apr.) 1984, pp. 878–885.
Durack, D. T., Clinical Aspect of Immunology, Blackwell Scientific Publications, London, 1982, pp. 1713–1751.
Henderson, E. S., Drug and Hematologic Reactions, Grune & Stratton, N.Y., 1974, pp. 207–221.
Rodriguez, V. & Bodey, G. P., Antibacterial Therapy, Clinics in Haematology, 5, 347–360, 1976.
Dale, D. C. et al, J. Clin Invest. 54, 664–671 (1974).
McCredie, K. B. et al, Clinics in Haematology, vol. 5, 379–394 (1976).
Motoyoshi, K. et al, Jap. J. Med. 21, 187–191 (1982).
Kohasaki, M. et al, Proc. Natl. Acad. Sci. USA, vol. 80, 3802–3806 (1983).

NOVEL CSF AND METHOD FOR OBTAINING THE SAME

FIELD OF THE INVENTION

The present invention relates to a colony stimulating factor (hereunder referred to as CSF) that has the ability to promote the differentiation and proliferation of bone marrow cells. More particularly, the invention relates to a novel CSF that has the ability to promote the differentiation and proliferation of human bone marrow cells to neutrophiles (such particular CSF may hereunder sometimes be referred to as human G-CSF) and a method for obtaining the same.

The CSF in accordance with the present invention has the potential for use not only as a curative for leukopenia but also as a reagent for clinical testing and research studies.

BACKGROUND OF THE INVENTION

CSF is a substance that acts on animal bone marrow cells so as to promote their differentiation and proliferation to macrophages or granulocytes. Several types of CSF have been reported. For example, Stanley, E. R. et al. reported that they purified from the urine of healthy adults a CSF that was composed of glycoprotein with a molecular weight of 45,000 and which exhibited a colony stimulating activity on mouse bone marrow cells but not on human bone-marrow cells (Fed. Proce., 35, pp. 2272–2278, 1975). Burgess, A. W. et al. reported that a CSF that would be effective in humans was partially purified from human placenta (Blood, 49, 573–583, 1977, and ibid, 54, 614–627, 1979). Shah, R. G. et al. reported the partial purification of a similar CSF from monocytes in human peripheral blood and PHA-stimulated lymphocytes (Blood, 50, pp. 811, 1977). Fojo, S. S. et al. reported the partial purification of a similar CSF from the supernatant of a culture of human lungs (Biochemistry, 17, pp. 3109–3116, 1978). All of these CSFs are glycoproteins having molecular weights in the range of 25,000 to 41,000 and they act directly on non-adherent human bone marrow cells to form colonies of neutrophiles, macrophages and eosinophiles. However, because of limitations on the available sources, completely purified CSFs have not yet been obtained. In addition to these CSFs recovered from normal human tissues, some kinds of human tumor cells have recently been reported to have the capability of CSF production. For instance, Asano, S. et al reported the recovery of CSF from lung cancer cells transplanted into nude mice (Blood, 49, pp. 845–852 reported CSF production from a cell line of mandibular squamous cell carcinoma and thyroid gland cancer cells (Cancer Res., 38, pp. 3910–3917, 1978; JNCI, 69, pp. 1235–1243, 1982; and J. Cell Physiol., 110, pp. 43–49, 1982). Wu, M. C. et al. reported CSF recovery from a pancreas cancer cell line (J. Biol. Chem., 254, pp. 6226–6228, 1979; J. Clin. Invest., 65, pp. 772–775, 1980). Dipersio, J. F. et al. reported that they recovered CSF from a GCT Cell line established from patients with malignant histiocytoma (Blood, 51, pp. 1068, 1978; and Blood, 56, pp. 717–727, 1980). Golde, D. W. et al. reported their recovery of CSF from an MO cell line established from patients with hairy cell leukemia (Blood, 52, pp. 1068–1072, 1978; and Blood, 57, pp. 13–21, 1981). The CSFs, which are effective on human bone marrow cells are glycoproteins having molecular weights ranging from 27,000 to 34,000 and isoelectric points (pI) of 4.5–5.7. The CSF obtained from the supernatant of a culture of GCT cell line has been purified to a specific activity of $1.12 \times 10^6$ U/mg. The specific acitivity of the CSF obtained from the supernatant of a culture of the MO cell line has been increased to $3.5 \times 10^6$ U/mg. However, none of these CSFs have been purified completely. In addition, CSF that has the ability to specifically promote the differentiation and proliferation of human bone marrow cells to neutrophiles has not been reported to date.

The present inventors have suceeded in establishing a novel cell line from tumor cells in patients with oral cancer. The cell line had a great ability to produce CSF and exhibited highly proliferative capabilities. Named CHU-1, this cell line has been deposited with Collection Nationale de Cultures de Microorganismes, (C.N.C.M.) Pasteur Institute, France on July 11, 1984 under Deposit Number I-315.

The present inventors cultured this CHU-1 in vitro and successfully isolated from the supernatant of the culture a highly pure CSF which exhibited a human neutrophilic colony stimulating activity, and which had a molecular weight of about 18,000 (as determined by sodium dodecylsulfate-polyacrylamide gel electrophoresis (SDS-PAGE)) and a specific activity of $3.94 \times 10^7$ U/mg or higher. In one aspect, the present invention relates to a CSF having the following physicochemical properties which are not shown in literature and makes this CSF a novel substance.

(i) Molecular weight:
$19,000 \pm 1,000$ as determined by sodium dodecylsulfatepolyacrylamide gel electrophoresis;

(ii) Isoelectric point:
Having at least one of the three isoelectric points, A, B and C, shown in Table 1:

TABLE 1

| Isoelectric point (pI) | In the presence of 4 M urea | In the absence of urea |
|---|---|---|
| A | 5.7 ± 0.1 | 5.5 ± 0.1 |
| B | 6.0 ± 0.1 | 5.8 ± 0.1 |
| C | 6.3 ± 0.1 | 6.1 ± 0.1 |

(iii) UV absorption:
Maximum absorption at 280 nm and minimum absorption at 250 nm;

(iv) The following 21 amino acids are arranged from N-terminal:

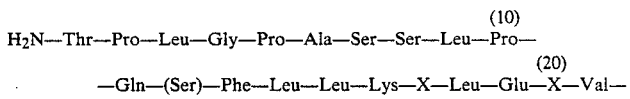

$$H_2N-Thr-Pro-Leu-Gly-Pro-Ala-Ser-Ser-Leu-Pro-$$
$$-Gln-(Ser)-Phe-Leu-Leu-Lys-X-Leu-Glu-X-Val-$$

In another aspect, the present invention relates to a method for obtaining a CSF, which comprises culturing a cell line having the ability to produce human G-CSF having the physicochemical properties shown above, subjecting the supernatant of the culture to steps (1) to (3) indicated below, and optionally subjecting the resulting fractions to either step (4) or (5):

(1) subjecting the supernatant of the culture to gel filtration using a gel having an effective fraction range of 5,000–70,000 daltons, and recovering fractions having the neutrophile-dominant colony stimulating activity (CSA);

(2) adsorbing the recovered fractions onto a carrier for reverse-phase high-performance liquid chromatography and performing elution by the density gradient technique with a mixture of water and an organic solvent so as to recover fractions having the neutrophile-dominant CSA;

(3) subjecting the so recovered fractions to high-performance molecular sieve chromatography so as to recover fractions having the neutrophile-dominant CSA;

(4) subjecting the so recovered fractions to isoelectric point electrophoresis so as to recover fractions having the neutrophile-dominant CSA; or (5) subjecting the fractions recovered in step (3) to the step of removing sialic acid so as to recover fractions having the neutrophile-dominant CSA.

Figure 1:
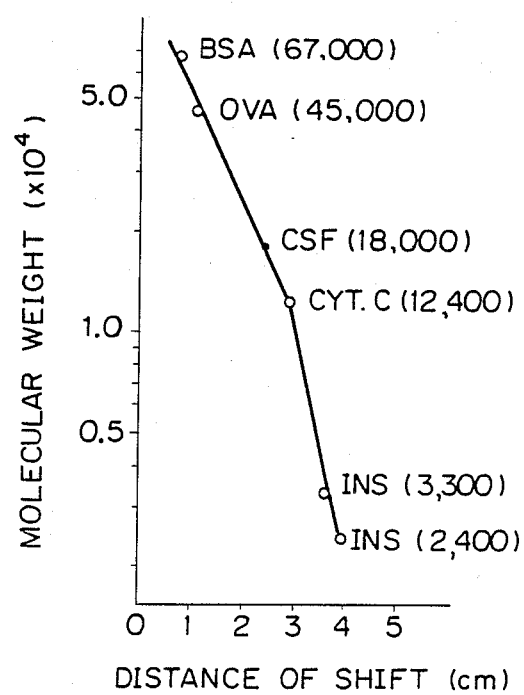
FIG. 1 shows the results of SDS-PAGE performed on the CSF of the present invention which is indicated by the dot in the graph.

An outline of the method for obtaining the CSF of the present invention is hereunder described by reference to CHU-1.

A sample of CHU-1 is suspended in an F-10 culture solution containing 10% of fetal calf serum (FCS) and subjected to rotary incubation in a glass roller bottle at a constant rate. When the inner wall of the roller bottle has been completely covered with CHU-1, the culture solution is replaced by FCS-free RPMI 1640, which is subjected to incubation for 4 days. To the recovered supernatant of the culture, FCS-containing F-10 culture solution is added again, and incubation is conducted for 3 days. The culture solution is again replaced by FCS-free RPMI 1640, and after incubation for 4 days, the supernatant of the culture is recovered. In accordance with this schedule, cycles of "incubation and recovery of the supernatant of serum-free culture" are repeated to obtain the final supernatant of culture of CHU-1. The supernatant thus obtained is subjected to ultrafilatration to obtain an approximately 1,000 -2,000—fold concentrate, which is subjected to gel filtration to recover fractions having the neutrophile-dominant CSA. The fractions are subjected to repeated purification by high-performance liquid chromatography, thereby recovering portions having the neutrophile-dominant CSA. The portions are subsequently freeze-dried.

For the purposes of the present invention, CSA was measured by one of the following two methods.

Measurements of CSA (a) Using human bone marrow cells:

Incubation on a monolayered soft agar culture was conducted in accordance with the method of Bradley, T. R. and Metcalf, D. (Aust. J. Exp. Biol. Med., Sci., 44, pp. 287-300, 1966). Fetal calf serum (FCS, 0.2 ml), a test sample (0.1 ml), a suspension of non-adherent human bone marrow cells (0.1 ml, containing $1-2 \times 10^5$ nuclear cells), modified McCoy's 5A culture solution (0.2 ml) and 0.75% agar containing modified McCoy's 5A culture solution (0.4 ml) were mixed and poured into a plastic dish (35 mm$\phi$) for tissue culture. After coagulanting the medium, incubation was conducted at 37° C. and 100% humidity with 5% $CO_2$/95% air. The number of colonies formed (one colony consisting of 50 or more cells) was counted after ten days of incubation, and the activity capable of forming one colony was taken as one unit of CSA.

(b) Using mouse bone marrow cells:

Horse serum (0.4 ml), a test sample (0.1 ml), a suspension of C3H/He (female). mouse bone marrow cells (0.1 ml, containing $0.5-1 \times 10^5$ nuclear cells) and 0.75% agar containing modified McCoy's 5A culture solution (0.4 ml) were mixed and poured into a plastic dish (35 mm$\phi$) for tissue culture. After coagulating the medium, incubation was conducted at 37° C. and 100% humidity with 5% $CO_2$/95% air for 5 days. The colonies formed was counted (one colony consisting of 50 or more cells), and the activity capable of forming one colony was taken as one unit of CSA.

The modified McCoy's 5A culture solution used in each of the methods (a) and (b) and the suspension of nonadherent human bone marrow cells used in method (a) were prepared by the following procedures.

Modified McCoy's 5A culture solution

Twelve grams of McCoy's 5A culture solution (product of Gibco Co.), 2.55 g of MEM amino acid/vitamin medium (product of Nissui Seiyaku Co., Ltd.), 2.18 g of sodium bicarbonate and 5,000 units of potassium penicillin G were dissolved in 500 ml of twice-distilled water, and the solution was sterilized by passage through a millipore filter (0.22 $\mu$m).

Suspension of non-adherent human bone marrow cells

Bone marrow cells obtained from a healthy adult by sternal puncture were diluted 5-fold with RPMI 1640 culture solution. The dilution was placed over Ficol-Paque solution (product of Pharmacia Fine Chmemicals), and the mixture was centrifuged at $400 \times g$ and 25° C. for 30 minutes to recover the interfacial cell layer (specific gravity < 1.077). The layer was washed with RPMI 1640 solution and the cell number was adjusted to a concentration of $5 \times 10^6$ cells/ml with RPMI 1640 culture solution containing 20% of FCS. The solution was poured into a 25 -$cm^2$ plastic flask for tissue culture. After incubation in a $CO_2$ incubator for 30 minutes, non-adherent cells were recovered from the supernatant and put into a plastic flask (25 $cm^2$). After a 2.5-hr incubation, non-adherent cells were collected from the supernatant.

When the CSF of the present invention was allowed to act on mouse bone marrow cells and human bone marrow cells as will be shown later in Example 6, stimulated formation of neutrophile colonies was observed. This clearly indicates that the CSF of the present invention is of the type that promotes the differentiation and proliferation of bone marrow cells to neutrophiles.

The following Reference Example is provided for describing the method of establishing CHU-1.

REFERENCE EXAMPLE (i) Tumor:

Pieces of tumor tissue from a patient with oral cancer accompanying a remarkable increase in the number of neutrophiles was transplanted into a nu/nu mouse. About 10 days after the transplantation, a remarkable increase in the size of the tumor and the number of neutrophiles was observed. 12 days from the transplantation, the tumor was aseptically extracted from the mouse and divided into small pieces (1-2 mm$^3$), which were subjected to the following incubations.

(ii) Primary culture:

Ten to fifteen tumor pieces were put into a 50-ml plastic centrifuge tube. After addition of 5 ml of a trypsin solution (0.25% trypsin and 0.02% EDTA), the mixture was shaken in a warm bath (37° C.) for 10 minutes. The supernatant was discarded and 5 ml of a trypsin solution having the same composition as used above was added and trypsin digestion was performed under agitation at 37° C for 15 minutes. A cell suspension was recovered and mixed with 1 ml of FCS so as to prevent the action of trypsin. The cell suspension was stored in ice bath.

The same procedure was repeated to recover a cell suspension which was combined with the previously obtained suspension and centrifuged at 1,500 rpm for 10 minutes to obtain cell pellets. The pellets were washed twice with F-10 culture solution containing 10% FCS and transplated in a plastic incubation flask (25 cm$^2$) to give a concentration of $5 \times 10^6$ cells/flask. The flask was incubated with F-10 culture solution containing 10% FCS for overnight in a $CO_2$ incubator (5% $CO_2$ and 100% humidity). The supernatant was removed together with non-adherent cells, and after addition of a fresh culture solution, incubation was continued. On the 6 day of the incubation, the cells was confluent and the culture medium was exchanged for a fresh one. On the next day, the culture solution wa discarded, and after addition of 2 ml of anti-mouse red blood cells (product of Oappel Corporation) that had been diluted 5-fold with RPMI 1640 and 2 ml of a guinea pig complement (product of Kyokuto Seiyaku Co., Ltd.) that had been diluted 2.5-fold with RPMI 1640, the mixture was incubated at 37° C. for 20 minutes. After completion of the incubation, the culture was washed twice with 10% FCS containing F-10 and the nu/nu mouse derived fibroblasts were removed. Subsequently, a F-10 culture solution containing 10% FCS was added and continued incubation.

Figure 4:
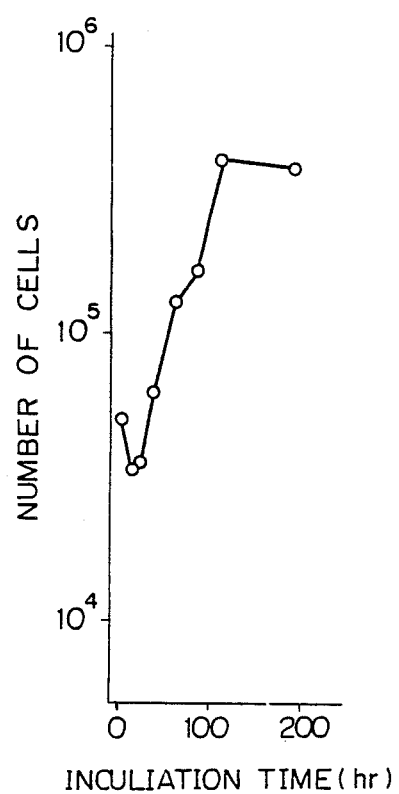
FIG. 4 shows the proliferation profile of CHU-1.

(iii) Subculture:

When the initial culture was completely filled with grown cells, it was replaced with F-10 culture solution containing 10% FCS and subculturing was carried out on the following day. After removing the culture solution with a Komagome's pipette, 2 ml of physiological saline solution containing 0.02% of preheated (37° C.) EDTA was added and heated on a hot plate at 37° C. for 2 minutes. Thereafter, the cells were detached by pipetting. After addition of 0.5 ml of FCS, the cell suspension was transfered into a 15-ml centrifuge tube and centrifuged at 1,500 rpm for 10 minutes to obtain cell pellets. The pellets were suspended in 1 ml of F-10 culture solution and divided into ten portions for subculturing The same procedures were repeated to perform subculturing at intervals of 4 or 5 days. The reproductive ability of the so obtained cells was examined by the following method. A suspension containing $5 \times 10^4$ cells/ml was prepared and twenty 1-ml layers of suspension were transplanted planted in a plastic dish (35 mm$_\phi$). During incubation in a $CO_2$ incubator, the dish was taken out at predetermined intervals and adherent cells were recovered and their number was counted. The results are shown in FIG. 4. About 20-24 hours after the cell implantation, cell multiplication started, with a mean duplicating time of about 20 hours.

The so obtained CHU-1 may be used as the cell line capable of producing the CSF of the present invention, which is hereunder described by Examples with reference to CHU-1. It should however be understood that the scope of the present invention is by no means limited to this CHU-1. For example, a microorganism strain or cell line which has been created by a recombinant DNA method is also applicable to this invention.

EXAMPLES

Example 1

Isolation of CSF

When two incubation flasks (150 cm$^2$) were completely filled with CHU-1, the cells were recovered and suspended in 500 ml of F-10 culture solution containing 10% FCS. The cell suspension was transferred into a 1580 cm$^2$ glass roller bottle (product of Belco Corporation) and subjected to rotary incubation at 0.5 rpm. When the inner wall of the bottle was completely covered with grown cells, the culture solution was replaced by serum-free RPMI 1640. After 4-day incubation, the supernatant of the culture was recovered and mixed with F-10 containing 10% FCS for performing continued incubation. After 3-day incubation, the culture solution was again replaced by serum-free RPMI 1640 and subjected to 4-day incubation, followed by recovery of the supernatant of the culture. By repeating the same procedures, a 500-ml of serum-free conditioned medium was obtained per bottle every week. This method enables a fairly prolonged cell maintenance and recovery of the conditioned medium.

To a single batch consisting of 5,000 ml of the recovered conditioned medium, Tween 20 was added at a concentration of 0.01% and the mixture was concentrated about 1000-fold by ultrafiltration using Hollow Fiber DC-4 and Amicon PM-10 (product of Amicon Corporation). The concentrated conditional medium was purified by the following sequence of steps.

(i) A portion (5 ml) of the concentrate was subjected to gel filtration on a Ultrogel AcA 54 column (4.6 cm diameter and 90 cm long, product of LKB Corporation) at a flow rate of about 50 ml/hr using 0.01 M Tris-HCl buffer (pH: 7.4) containing 0.15 M NaCl and 0.01% Tween 20 (product of Nakai Kagaku K.K.). The column had been calibrated with bovine serum albumin (mol. wt. 67,000), ovalbumin (mol. wt. 45,000) and cytochrome C (mol. wt. 12,400). After the gel filtration, a 0.1-ml portion was sampled from each of the fractions and diluted 10-fold. The activity of each fraction was checked by the "method (b) for determination of CSA". Fractions having Ve = 400 - 700 ml showed macrophage-dominant CSA while fractions having Ve=8-00–1,200 ml exhibited granulocyte-dominant CSA. Therefore, the fractions of the second group were combined and concentrated to a volume of about 5 ml by ultrafiltration using PM-10 (product of Amicon Corporation).

(ii) To the concentrated fractions, a 0.1% aqueous solution of trifluoroacetic acid containing 30% of n-propanol (amino acid sequencing grade, product of Tokyo Kasei K.K.), was added and the mixture was left to stand in ice for about 15 minutes. Thereafter, the mixture was centrifuged at 15,000 rpm for 10 minutes to remove the precipitate. Then, he supernatant was passed through a micro Bondapak C18 column (semi-preparatory column produced by Waters Associates, Inc.) that had been equilibrated with an aqueous solution containing n-propanol of the amino acid sequencing grade and triflouoroacetic acid. The column was developed by linear gradient elution with 30–60% of n-propanol containing 0.1 of trifluoroacetic acid. A high-performance liquid chromatograph apparatus (Model 685-50 of Hitachi, Ltd.) together with a detector (Model 638-41 of Hitachi, Ltd.) was used for the purpose of simultaneous measurement of absorptions at 220 nm and 280 nm. After elution, a 10-ml portion was separated from each of the fractions and diluted 100-fold. The activity of each fraction was checked by the "method (b) for determination of CSA". The peaks eluted with 40% n-propanol were found to have the neutrophile-dominant CSA so these peaks were collected and subjected to high-performance liquid chromatography under the same conditions as were used above. When the fractions were checked for CSA by the same method as above, it was again confirmed that the peaks corresponding to 40% n-propanol had the neutrophile-dominant CSA. Therefore, four fractions (4 ml) of such peaks were collected and freeze-dried.

(iii) The freeze-dried powder was dissolved in 200 μl of a 40% n-propanol containing 0.1% trifluoroacetic acid, and the solution was subjected to highperformance liquid chromatography on a TSK-G-3000 SW column (2.5 mm×60 cm, product of Toyo Soda Manufacturing Co., Ltd.). Elution was carried out at 0.4 ml/min with 40% n-propanol containing 0.1% trifluoroacetic acid. With the aid of a fraction collector (FRAC-100 of Pharmacia Fine Chemicals), 0.4-ml fractions were collected. The recovered fractions were checked for their CSA by the same method as used above, and fractions having retention times of 37–38 minutes (corresponding to a molecular weight of ca. 20,000) were found to have the neutrophile-dominant CSA. Therefore, these fractions were pooled and purified with an analytical micr Bondapak C 18 column (4.6 mm×30 cm). Thereafter, the main peaks were recovered and freeze-dried.

Example 2

Physiological Properties

The physicochemical properties of the CSF of the present invention which was prepared in Example 1 were determined by the following analyses and tests.

(i) Molecular weight (a) The molecular weight of the CSF was determined by sodium dodecylsulfate-polyacrylamide gel electrophoresis (SDS-PAGE). The electrophoretic equipment was Model GE-2/4 (Pharmacia Fine Chemicals) and the gel was made up of a polyacrylamide slab gel (T=15% and C =2.6%) measuring 70 mm×70 mm×3 mm, and a concentrating gel (T =3%, C=20%). A modified CSF sample was prepared by the following procedure: CSF was boiled for 3 minutes in a solution containing 2% of sodium dodecylsalfate in 0.64 M 2-mercaptoethanol, and urea was then added to the solution at a final concentration of 4 M. After performing electrophoresis on 2 μg of the sample at 120 volts for 3 hours, the gel was removed and fixed with methanol:acetic acid:water (4:1:5) and stained for band detection using Silver Stain (product of Bio-Rad Corporation). Bovine serum albumin (BSA, mol. wt. 67,000), ovalbumin (OVA, mol. wt. 45,000), cytochrome C (Cyt. C, mol. wt. 12,000) and insulin (Ins., mol. wt. of A chain: 3,300, mol. wt. of B chain: 2,400) were used as molecular weight markers after similar treatments. A single band corresponding to a molecular weight of approximately 18,000 was detected. The results of molecular weight measurement are shown in FIG. 1.

Figure 5:
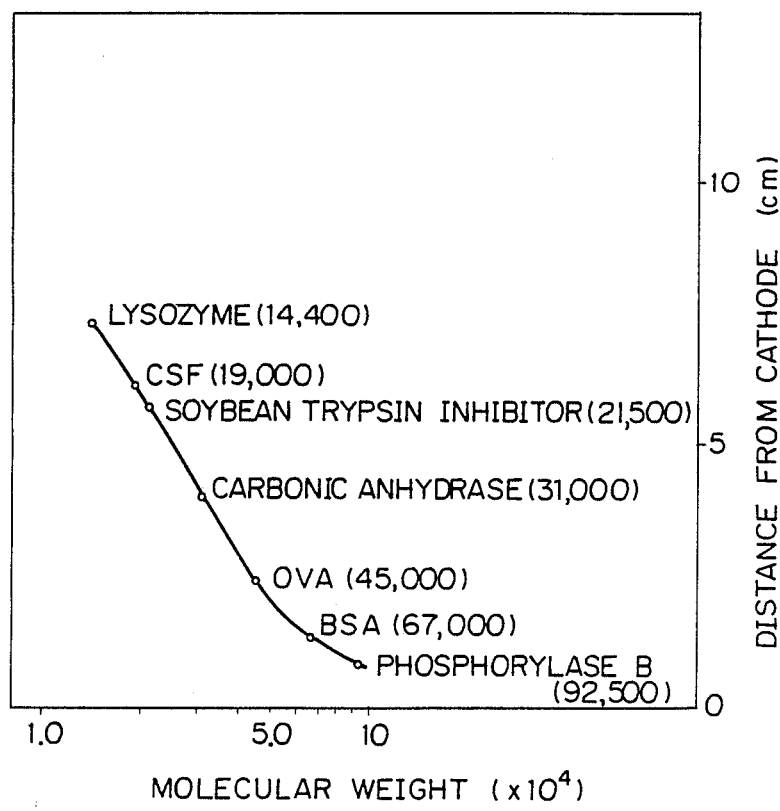
FIG. 5 is another graph showing the results of SDS-PAGE performed on the CSF of the present invention which is indicated by the dot in the graph.

(b) The molecular weight of the CSF was determined by sodium dodecylsulfate-polyacrylamide gel electrophoresis (SDS-PAGE), but this time the electrophoretic equipment was PROTEAN®(16 cm, Product of Bio-Rad Corporation), using a gel made up of a polyacrylamide slab gel (T=15%, C=2.6%) measuring 140 mm×160 mm×1.5 mm, and a concentrating gel (T=3%, C=20%). A denatured CSF sample was prepared by the following procedure: CSF was boiled for 3 minutes in a solution containing 2% of sodium dodecylsulfate in 0.46M 2-mercaptoethanol. After performing electrophoresis on 4 μg of the sample with a constant current of 30 mA for 4 hours, the gel plate was removed and stained with 0.25% Coumasy Brilliant Blue R 250 (product of Sigma Chemical Co.) for band detection. The following substances were used as molecular weight markers after similar treatments: phosphorylase B (mol. wt. 92,500), bovine serum albumin (BSA, mol. wt. 67,000), ovalbumin (OVA, mol. wt. 45,000), carbonic anhydrase (mol. wt. 31,000), soybean trypsin inhibitor (mol. wt. 21,500) and lysozyme (mol. wt. 14,400). A single band corresponding to a molecular weight of approximately 19,000 was detected. The results of molecular weight measurement are shown in FIG. 5. (c) In view of the results (a) and (b), the CSF of the present invention is deemed to have a molecular weight of 19,000±1,000 as determined by SDS-PAGE.

(ii) Isoelectrcc point

The isoelectric point of the CSF of the present invention was determined by a flat bed, isoelectric electrophoretic apparatus, FBE-3000 (product of Pharmacia Fine Chemicals). After 2-hr electrophoresis with a constant power of 30 watts (Vmax=2,000 volts) on a polyacrylamide gel (T=5%, C=3%, 115 mm×230 mm) containing Pharmalyte (pH=4–6.5, Pharmacia Fine Chemicals) and 4M urea, the CSF was fixed with 30% methanol/10% trichloroacetic acid/35% sulfosalicylic acid, and stained with Coumasy Brilliant Blue R-250. A Low pI kit (pH: 2.5–6.5, product of Pharmacia Fine Chemicals) was used as an isoelectric point marker.

Figure 2:
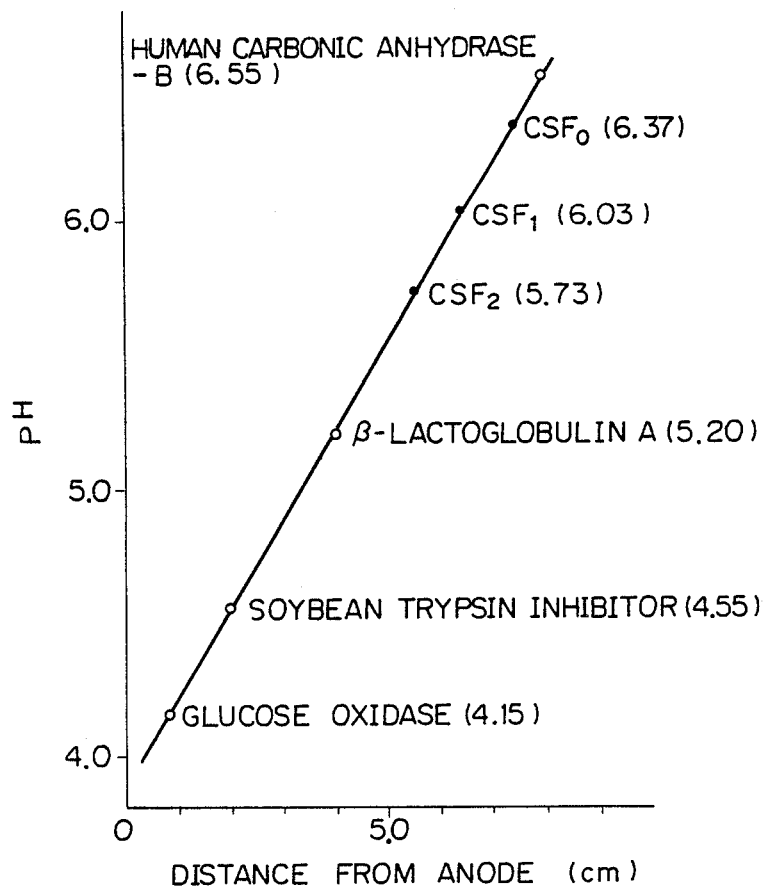
FIG. 2 shows the results of isoelectric electrophoresis performed on the CSF of the present invention in the presence of 4M urea.

Observation of band separation in the pH range of 4 to 6.5 gave three distinct bands corresponding to pI=5.73, 6.03 and 6.37, among which the two bands for pI=5.73 and 6.03 were predominant components. The results of measurement are shown in FIG. 2, wherein $CSF_0$, $CSF_1$ and $CSF_2$ denote CSFs according to the present invention having different isoelectric points. Isoelectric electrophoresis in the absence of urea produced three bands corresponding to pI=5.52, 5.80 and 6.13.

Ten measurements of isoelectric point were conducted by the method described above and the results are shown in Table 1, which lists three isoelectric points, A, B and C, differing from each other by about 0.3.

In order to see whether there was any correlation between the three bands of isoelectric point and the values of CSA, the CSF which was just purified with TSK-G 3000 SW column in Example 1 (iii) was subjected to band separation with a preparative isoelectric electrophoresis apparatus, Model FBE-3000 of Pharmacia Fine Chemicals. The band separating conditions used were as follows.

Sample: A freeze-dried sample of CSF (500 μg) was dissolve in 1 ml of 0.05N phosphoric acid containing 4M urea.

Support: To 15 g of Sephadex-IEF (product of Pharmacia Fine Chemicals), 225 ml of twice-distilled water containing 4M urea and 0.1% Tween 20 was added. After addition of 12 ml of Pharmalyte (pH: 4–6.5, product of Pharmacia Fine Chemicals), the mixture was left to stand overnight until it swelled. Thereafter, the mixture was thoroughly deaerated in a sucking bottle and poured on a glass plate (230 mm×230 mm) to form a uniform gel layer in a thickness of 5 mm. The gel layer was removed from the plate except for the most uniform portion covering an area of 50 mm×230 mm.

Electrode solutions:

Electrode strips (6×10 mm, product of Pharmacia Fine Chemicals) were impregnated with 0.1 M phosphoric acid (anode) and 0.1 M NaOH (cathode). One strip was placed parallel to one end of the gel, and the other strip was likewise placed parallel to the other end of the gel. The electrodes were connected to a constant power supply ECPS 2000/300, product of Pharmacia Fine Chemicals.

Preliminary electrophoresis:

45 minutes at 8 watts.

Addition of sample:

A gel having a width of 1 cm was scraped at a position 5 cm away from the anode end and replaced in the initial position after mixing with a sample solution.

Electrophoresis:

4 hours at 50 watts furnished from the constant power supply, ECPS 2000/300.

After completion of the electrophoresis, the gel plate was taken out of the tank and divided into 26 fractions with a fractionating grid. After measuring the pH of each of the fractions, the gel scraped from each fraction was transferred into a polypropylene mini-column (Muromac of Muromachi Kagaku K.K.) and subjected to extraction with 4 ml of 4M guanidine hydrochloride containing 0.1% of trifluoroacetic acid. A of the extracted fractions was diluted portion (5 μl) of each of the extracted fractions was diluted with 2 ml of RPMI 1640 culture medium containing 1% bovine serum albumin and checked for its CSA by the "method (b) for CSA determination". Each of the fractions eluted contained three active peaks which agreed well with the previously mentioned three isoelectric points pI =5.73, 6.03 and 6.37.

In order to check whether the differences in isoelectric point should be ascribed to the peptide portion of CSF or the sugar chain (especially, the number of additions of sialic acid), two CSF samples, one treated with neuraminidase and the other untreated with neutraminidase, were subjected to electrophoresis. Three bands were observed in the untreated sample but only a single band for pI =6.37 was observed in the neuraminidase-treated sample. Isoelectric electrophoresis was also conducted for a CSF sample that was dissolved in an aqueous solution of 6M guanidine hydrochloric acid, followed by pH adjustment to 1.5 with 1N HCl add standing at 80° C. for 120 minutes. Band shifts that occurred in this treated sample were the same as those occurring in the neuraminidase-treated sample. The neuraminidase treatment caused no injury to CSA. These results seem to suggest that the differences in isoelectric point of CSF are probably due to the difference in the number of additions of sialic acid.

(iii) UV absorption

Figure 3:
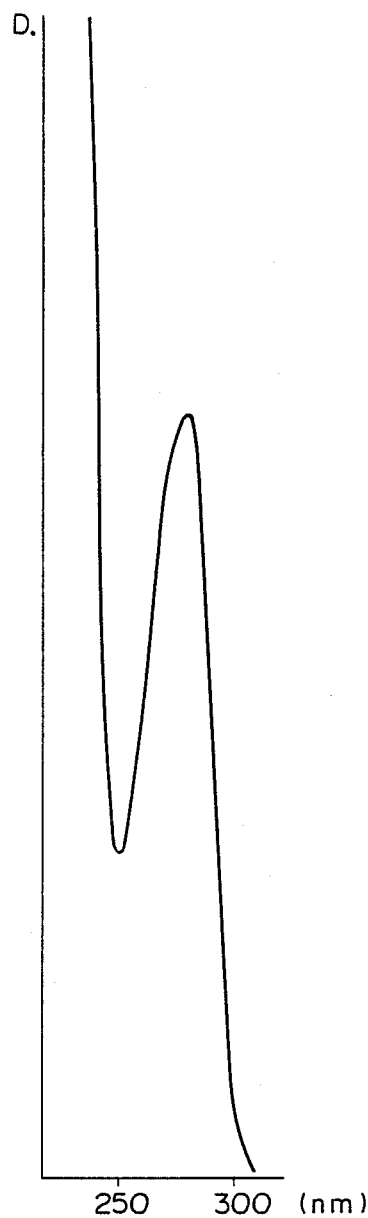
FIG. 3 is a UV absorption spectrum chart for the CSF of the present invention.

The sample was checked for its UV absorption with a spectrophotometer, with 0.1% trifluoroacetic acid containing 40% of n-propanol being taken as a reference. As shown in FIG. 3, a maximum peak occurred at 280 nm and a minimum peak at 250 nm.

(iv) Amino acids in the protein portion

The sample was hydrolyzed by a conventional method and analyzed for the amino acid composition of the protein portion with an automatic amino acid analyzer, Model 835 of Hitachi, Ltd. The results are shown in Table 2. The hydrolysis was conducted under the following conditions.

(a) 6N HCl, 110° C. ×24 hr in vacuuo, (b) 4N methanesulfonic acid +0.2% 3-(2-aminoethyl-)indole, 110° C×24, 48 or 72 hr, in vacuuo.

Each of the samples was dissolved in a solution (1.5 ml) containing 40% n-propanol and 0.1% trifluoroacetic acid. Portions (0.1 ml) of the solutions were dried with dry $N_2$ gas and mixed with reagent (1) or (2) for hydrolysis in fused test tubes in vacuuo.

Each of the "Measured values" in Table 2 was a mean of four values, i.e., the 24-hr value for (1) and 24-,, 48 - and 72-hr values for (2). The amounts of Thr, Ser, ½Cys, Met, Val, Ile and Trp were calculated by the following methods (see, Seikagaku Jikken Koza, Tanpakushitsu Kagaku II, published by Tokyo Kagaku Dojin):

(a) Measurements were made of the time-dependent changes of the 24-, 48- and 72-hr values for Thr, Ser, 178Cys and Met after hydrolysis with (2) and the data were extrapolated for zero hour.

(b) Measurements were made of the 72-hr values for Val and Ile after hydrolysis with (2).

(c) Measurements were made of the 24-, 48- and 72-hr values for Trp after hydrolysis with (2), and these values were averaged.

The values shown in the column of "Predicted Number of Residual Amino Acid Groups" are based on the assumption of the existence of 33 Leu's. Generally, the amino acids that require correction of the type described above are either destroyed partly or considerably during hydrolysis or refractory to hydrolysis. In particular, Pro produces a low color yield. Primarily for these reasons, the actually measured contents (nmol) of amino acids of interest and hence, the calculated number of each of the residues, has a tendency to be lower than theoretical values (see Seikagaku Jikken Koza, ibid).

TABLE 2

| Amino acids | Measured values (nmol) | Predicted number of amino acid residues (rounded to the parenthesized integrals) | |
|---|---|---|---|
| Asp (Asp + Asn) | 3.54 | 4.3 | (4) |
| Thr | 4.58 | 5.5 | (6) |
| Ser | 10.64 | 12.9 | (13) |
| Glu (Glu + Gln) | 22.31 | 27.0 | (27) |
| Pro | 8.30 | 10.1 | (10) |
| Gly | 10.60 | 12.8 | (13) |
| Ala | 14.85 | 18.0 | (18) |
| ½Cys | 2.59 | 3.1 | (3) |
| Val | 6.16 | 7.5 | (7) |
| Met | 2.26 | 2.7 | (3) |
| Ile | 3.29 | 4.0 | (4) |
| Leu | 27.24 | 33.0 | (33) |
| Tyr | 2.60 | 3.1 | (3) |
| Phe | 5.08 | 6.1 | (6) |
| Lys | 3.68 | 4.5 | (4) |
| His | 3.93 | 4.8 | (5) |
| Trp | 1.61 | 1.9 | (2) |
| Arg | 4.29 | 5.2 | (5) |
| Total | | | (166) |

TABLE 2-continued

| Amino acids | Measured values (nmol) | Predicted number of amino acid residues (rounded to the parenthesized integrals) |
|---|---|---|
| Calculated molecular weight (no sugar counted in 166 residues) | | 17961 |

(v) Temperature stability

A freeze-dried CFS sample (1 mg) was dissolved in 4 ml of 0.1% trifluoroacetic acid containing 40% of n-propanol. A portion (1 ml) of the solution was diluted with 10 ml of 0.01M Tris-HCl buffer (ph: 7 4) containing 1% bovine serum albumin to give a CSF concentration of 25 ng/ml. Five more dilutions of the sample were prepared in the same manner as described above, and the total of six dilutions were treated for 40 minutes at varying temperatures, 0,37,45,56,65 and 100° C. Determination of the residual CSA in each of the samples showed that the CSF of the present invention was stable at 0 - 45° C. and became inactivated at 56° C.

(vi) pH stability

A freeze-dried CSF sample (1 mg) was dissolved in 4 ml of 0.1% trifluoroacetic acid containing 40% of n-propanol. Portions (1 ml) of the solution were diluted with 10-ml solutions containing 1% bovine serum albumin which were buffered at pHs of 1, 3, 5, 7, 9, 11 and 13. After adjusting the CSF concentration to 25 ng/ml, tee dilutions were left to stand in ice for 24 hours. Thereafter, 2 ml of each dilution was dialyzed against a 0.01M Tris-HCl buffer (pH: 7.4) and examined in relation to the residual CSA. The CSF of the present invention was found to be stable over a broad pH range of 1 to 11.

(vii) Enzyme stability

A freeze-dried CSF sample was dissolved in 0.1% trifluoroacetic acid containing 40% n-propanol and four specimens were prepared by mixing 0.67 μg of the solution with 0.05 M Tris-HCl buffer (pH: 8.0) to make a total of 1 ml. Another specimen was prepared by mixing 0.67 ug of the trifluoroacetic acid solution with 0.05M acetate buffer (pH: 5.0) to make a total of 1 ml. To three of the first four specimens, RNase, trypsin and pronase were added in amounts of 1 μg, whereas the fourth specimen was used as a control. To the fifth specimen, 1 μg of neuraminidase was added. The five specimens were reacted at 37° C. for 2 hours. After completion of the reaction, 0.1-ml portions were taken out of the specimens and diluted with 1 ml of RPMI 1640 culture solution containing 1% bovine serum albumin. CSA inspection showed that the CSF of the present invention was not inactivated by RNase or neuraminidase but was inactivated by trypsin and pronase.

(viii) Sugar composition

A sample (11 nmol) was mixed with 25 nmol of inositol as an internal standard and 500 μl of 1.5 N HCl-methanol, and then subjected to reaction at 90° C. for 4 hours in a $NO_2$ purged fused tube. After completion of the reaction, the tube was opened at an end and supplied with silver carbonate ($Ag_2CO_3$) for neutralization. After addition of acetic anhydride (50 μl) and shaking, the mixture was left to stand in a dark place overnight at room temperature. The upper layer was placed into a sample tube and dried with $N_2$ gas On the other hand, the precipitate was washed with freshly added methanol and lightly centrifuged. The upper layer was poured into the sample tube which had been dried with $N_2$ gas, and dried again. To the dried content, 50 μl of a TMS reagent (5:1:1 mixture of pyridine, hexamethyl disilazane and trimethylchlorosilane) was added and after reaction at 40° C. for 20 minutes, the mixture was stored in a deep freezer. The same procedures were followed except that the internal standard was the combination of 25 nmol of inositol and 50 nmol of one other sugar such as galactose (Gal), N-acetylgalactosamine (Gal NAc) and sialic acid.

The samples prepared were subjected to gas chromatography under the following conditions.

Assay conditions

Column: 2% OV-17 Vinport HP (60–80 mesh), 3 m, glass

Temperature: elevated to a temperature between 110° C. and 250° C. at a rate of 4° C/min Carrier gas pressure: 1.2–1.6 $kg/cm^2$ $N_2$ in the initial stage, and 2–2.5 $kg/cm^2$ $N_2$ toward the end of assay Sensitivity: $10^3$ megaohm for a range of 0.1–0.4 volts Pressure 0.8 $kg/cm^2$ $H_2$, and 0.8 $kg/cm^2$ air Sample feed: 2.5–3.0 μl Analysis showed that the CSF of the present invention was composed of three sugars, galactose, N-acetylgalactosamine and sialic acid.

(ix) Determination of amino acid sequence

A sample was subjected to Edman's decomposition in a gas-phase sequenator (product of Applied Biosystem, Inc.), and the PTH amino acid obtained was assayed by conventional techniques using a high-performance liquid chromatograph (product of Beckman Instruments, Inc.) and an Ultrophere-ODS column (product of Beckman Instruments, Inc.). The column (5 μm, 4.6 mm$^\phi$ and 250 mm$^L$) was first equilibrated with a starting buffer (15 mM sodium acetate buffer, pH=4.5, an aqueous solution containing 40% acetonitrile). Then, a sample as dissolved in 20 μl of the starting buffer was subjected to amino acid separation by isocratic elution with the starting buffer. The flow rate was 1.4 ml/min and the column temperature was held at 40° C. Detection of the PTH amino acid was realized by using UV absorption at 269 nm and 320 nm. Samples (2 nmol) of standard PTH amino acid (Sigma Chemical Co.) that had been subjected to amino acid separation in the same system for determination of retention times were used as references against which the retention times for the specimen were compared in order to identify the amino acid sequence. The arrangement of 21 amino acids from N terminal was as follows:

(10)
H$_2$N—Thr—Pro—Leu—Gly—Pro—Ala—Ser—Ser—Leu—Pro—

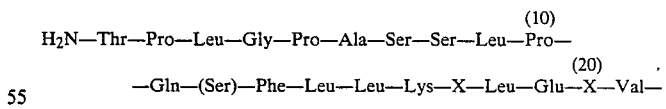

Example 3

Determination of Specific Activity

The specific activities of the CSFs of Example 1 for human bone marrow cells were measured by the "method (a) for CSA determination". The result was $3.94 \times 10^7$ U/mg or higher.

Example 4

The freeze-dried powder of CSFs prepared in Example 1 was separated into individual CSF components in terms of differences in isoelectric point as determined by preparative isoelectric electrophoresis under the following conditions.

Equipment: FBE-3000 (product of Pharmacia Fine Chemicals)

Sample: 10 mg of the freeze-dried powder was dissolved in 2 ml of 0.05 N phosphoric acid containing 4M urea.

Support: To 15 g of Sephadex-IEF (product of Pharmacia Fine Chemicals), 225 ml of twice-distilled water containing 4M urea and 0.1% Tween was added. After addition of 12 ml of Pharmalyte (pH: 4–6.5, product of Pharmacia Fine Chemicals), the mixture was left to stand overnight until it swelled. Thereafter, the mixture was thoroughly deaerated in a sucking bottle and poured on a glass plate (230 mm×230 mm) to form a uniform layer in a thickness of 5 mm.

Electrode solutions:

Electrode strips (6×10 mm, product of Pharmacia Fine Chemicals) were impregnated with 0.1 M phosphoric acid (anode) and 0.1 M NaOH (cathode). One strip was placed parallel to one end of the gel and the other strip was likewise placed parallel to the other end of the gel. The electrodes were connected to a constant power supply ESPS 2000/300, product of Pharmacia Fine Chemicals.

Preliminary electrophoresis:

45 minutes at 8 watts

Addition of sample:

A gel having a width of 1 cm was scraped at a position 5 cm away from the anode and replaced in the initial position after mixing with a sample solution.

Electrophoresis:

4 hours at 50 watts furnished from the constant power supply, ECPS 2000/300.

After completion of the electrophoresis, the gel plate was taken out of the tank and divided into 26 fractions with a fractionating grid. After measuring the pH of each of the fractions, the gel scraped from each fraction was transferred into a polypropylene mini-column (Muromac of Muromachi Kagaku K.K.) and subjected to extraction with a 0.1% aqueous trifluoroacetic acid solution (10 ml) containing 4M guanidine hydrochloride. A portion (5 μl) of each of the extracted fractions was diluted with 16 ml of RPMI 1640 culture solution containing 1% bovine serum albumin and checked for its CSA by the "method (b) for determination". Each of the fractions exhibited activity peaks in substantial agreement with three different isoelectric point peaks pI=5.73, 6.03 and 6.37. The respective active fractions were adsorbed on a micro Bondapak C 18 column (Waters Associates, Inc., the semi-preparatory grade, 8 mm×30 cm) that had been equilibrated with an aqueous solution containing n-propanol and trifluoroacetic acid. The fractions were then eluted with a 0.1% aqueous trifluoroacetic acid solution containing n-propanol having a linear concentration gradient of 30–60%. The peaks eluted with 40% n-propanol were recovered and freeze-dried.

The amino acids in the recovered fractions and their sequence were examine by the methods used in Example 2(iv) and (ix). The results were in agreement with those obtained in Example 2.

Example 5

A portion (10 mg) of the freeze-dried CSF powder prepared in Example 1 was dissolved in 2 ml of a mixture (pH: 9.0) of 0.1M sodium carbonate and sodium bicarbonate. The pH of the solution was adjusted to 5.0 with 1N HCl. After addition of 100 μg of neuraminidase, the mixture was subjected to reaction at 37° C. for 2 ours, and the reaction mixture was adsorbed on a micro Bondpack C. 18 column (Waters Associates, Inc., the semi-preparatory grade, 8 mm×30 cm) that had been equilibrated with an aqueous solution containing n-propanol and trifluoroacetic acid. The adsorbed mixture was eluted with a 0.1% aqueous solution of trifluoroacetic acid containing n-propanol having a linear concentration gradient of 30- 60%. The peaks eluted with 40% n-propanol were recovered and freeze-dried. Part of the dried powder was subjected to analytical isoelectric electrophoresis, producing a single band corresponding to pI=6.37.

Example 6

Colony Classification

Colonies formed in accordance with the "method (a) for CSA determination" were transferred, together with an agar layer, onto a slide glass by the method of Kubota, K. et al. (Exp. Hemat., 8, pp. 339–344, 1980), and dried to prepare a specimen in a film form. This specimen was subjected to colony classification by both esterase double staining and Bieblich scarlet staining in accordance with the method of Konwalinka, G. et al. (Exp. Hemat., 8, pp. 434–440, 1980). Details of the method of Konwalinka, G. et al are described below.

(1) Fixing solution: buffered formalin/acetone solution (ph: 6.6)

| | | |
|---|---|---|
| Na$_2$HPO$_4$ | 20 mg | |
| KH$_2$PO$_4$ | 100 mg | |
| H$_2$O | 30 ml | |
| Acetone | 45 ml | |
| Formalin | 25 ml | |
| Total | 100 ml | (stored at 4° C.) |

(2) Non-specific esterase dying reaction solution (prepared just before use) composed of a filtered mixture of the following components (A) and (B):

| | | |
|---|---|---|
| (A) | Phosphate buffer (1/15 mol/1,000 ml, pH: 6.3) | 9.5 ml |
| | Fast Garnet BGC salt | 10 mg |
| (B) | α-naphthyl butyrate | 10 mg |
| | Ethylene glycol monomethyl ether | 0.5 ml |

(3) Chloroacetate esterase dying reaction solution (prepared just before use) composed of a filtered mixture of the following components (A) and (B):

| | | |
|---|---|---|
| (A) | Phosphate buffer (1/15 mol/1,000 ml, pH: 7.4) | 9.5 ml |
| | Fast Blue RR salt | 5 mg |
| (B) | Naphthol AS-D chloroacetate | 1 mg |
| | N,N—dimethylformamide | 0.5 ml |

(4) Bieblich Scarlet dying reaction solution composed of a mixture of 2 ml of solution (A) and 98 ml of solution (B):

| | | |
|---|---|---|
| (A) | Bieblich Scarlet (product of MC/B Corporation) | 5 g |
| | Dimethylsulfoxide | 100 ml |
| (B) | 0.1 M Tris-HCl buffer (pH: 7.4) | |

Using the thus prepared fixing solution and reaction solutions, colony staining was effected in the following order.

(i) The colonies were fixed for 30 seconds with the fixing solution (1) at 4–10° C., washed with distilled water three times and dried at room temperature for 10–30 minutes.

(ii) The dried colonies were immersed in the reaction solution (2) at room temperature for 20–30 minutes and washed with distilled water three times.

(iii) The colonies were immersed in the reaction solution (3) at room temperature for 15 minutes and washed with distilled water three times.

(iv) The colonies were immersed in the reaction solution (4) at room temperature for 2 hours and washed under flushing water.

(v) The colonies were dried and observed. Cells containing blue granules were classified as neutrophiles; those containing brow granules were classified as granulocyte-macrophages and those containing red granules were classified as eosinophiles.

At days 7, 10 and 14 of the incubation, the colonies formed by using the CSF of the present invention were entirely composed of chloroacetate esterase positive neutrophiles and no other colony types were found.

ADVANTAGES OF THE INVENTION

From the following results of experiment (1) to (5), the CSF of the present invention was found to have been substantially purified: (1) it exhibited a single peak both in reverse-phase and molecular sieve high-performance liquid chromatographic analyses, and the peak was in agreement with the activity peak; (2) the CSF gave a single band in SDSPAGE: (3) the CSF was separated into components having three different isoelectric points upon isoelectric electrophoresis, but each component was a single component exhibiting CSA; a sample that had been freed from a terminal sialic acid either by enzymatic or chemical techniques gave a single band in isoelectric electrophoresis; (4) only a single type of PTH amino acid appeared in each of the steps involved in analysis of the sequence of 21 amino acid residues from N terminal; and (5) in terms of specific activity, the CSF is about 10 times as pure as those CSFs so far reported as being effective in humans.

Such a highly purified form of CSF, especially one which is highly purified and has the ability to promote the differentiation and proliferation of bone marrow cells to human neutrophiles, is not to be found in available literature. The CSF of the present invention is obtainable from a genetically engineered human G-CSF producing strain. In addition to use as a reagent for clinical testing or research studies, the CSF of the present invention may potentially be used as a curative for serious infections diseases so far incurable by antibiotics because it has various capabilities, i.e. promotion of the proliferation of the cells of a transplanted bone marrow, promotion of the restoration of radiation exposed bone marrow tissues, promotion of the restoration of the leukocyte level after application of cancer control agents, and promotion of the differentiation and proliferation of bone marrow cells to neutrophiles.

What is claimed is:

1. Biologically active human G-CSF characterized by a molecular weight in the range of about 18,000 to 20,000 daltons on SDS PAGE, a specific activity of at least about $3.94 \times 10^7$ u/mg, an isoelectric point selected from the group consisting of (A) $5.7 \pm 0.1$ in the presence of 4M urea and $5.5 \pm 0.1$ in the absence of urea;

(B) $6.0 \pm 0.1$ in the presence of 4M urea and $5.8 \pm 0.1$ in the absence of urea, and (C) $6.3 \pm 0.1$ in the presence of 4M urea and $6.1 \pm 0.1$ in the absence of urea, a UV absorption maximum at 280 mn and a minimum at 250 nm, said G CSF having the ability to promote differentiation and proliferation of bone marrow cells specifically into neutrophiles and having a protein N terminal sequence Thr-Pro-Leu-Gly-Pro-Ala-Ser-Ser-Leu-Pro-Gln-Ser-Phe-Leu-Leu-Lys-Cys-Leu-Glu-Gln-Val.

2. The human G-CFS of claim 1 characterized by having an isoelectric point of $5.7 \pm 0.1$ in the presence of 4M urea and $5.5 \pm 0.1$ in the absence of urea.

3. The human G-CFS of claim 1 characterized by having an isoelectric point of $6.0 \pm 0.1$ in the presence of 4M urea and $5.8 \pm 0.1$ in the absence of urea.

4. The human G-CSF of claim 1 characterized by having an isoelectric point of $6.3 \pm 0.1$ in the presence of 4M urea and $6.1 \pm 0.1$ in the absence of urea.

5. A pharmaceutical composition for the treatment of leukopenia comprising a therapeutically effective amount of G-CSF of claim 1,2, 3 or 4 in pharmaceutically acceptable carrier.

* * * * *

UNITED STATES PATENT AND TRADEMARK OFFICE
CERTIFICATE OF CORRECTION

PATENT NO. : 4,833,127

DATED : May 23, 1989

INVENTOR(S) : Masayoshi Ono and Hitoshi Nomura

It is certified that error appears in the above-identified patent and that said Letters Patent is hereby corrected as shown below:

Column 2, line 12, after line, insert --, named CHU-1,--.

Column 2, line 14, delete -- "Named" --.

Column 2, lines 15-18, delete in its entirety.

Column 6, line 4, after the period insert --CHU-1 was later alternatively called CHU-2. Under the latter designation, it has been deposited with Collection Nationale de Cultures de Microorganismes (C.N.C.M.) Pasteur Institute, France, on September 12, 1985 under Deposit Number I-483.--

UNITED STATES PATENT AND TRADEMARK OFFICE
CERTIFICATE OF CORRECTION

PATENT NO. : 4,833,127

DATED : May 23, 1989

INVENTOR(S) : Masayoshi Ono, et. al.

It is certified that error appears in the above-identified patent and that said Letters Patent is hereby corrected as shown below:

Column 6, line 8, after the period insert --A further example is the cell line deposited with C.N.C.M. on July 11, 1984 under Deposit Number I-315. A replacement I-315 deposit was made on August 1, 1991 in response to a requirement dated July 22, 1991 by C.N.C.M. based on C.N.C.M.'s inability to supply samples uncontaminated with mycoplasma.--

Signed and Sealed this

Twenty-third Day of March, 1993

Attest:

STEPHEN G. KUNIN

*Attesting Officer*   *Acting Commissioner of Patents and Trademarks*